(12) United States Patent
Maeshima et al.

(10) Patent No.: US 6,191,849 B1
(45) Date of Patent: Feb. 20, 2001

(54) WAFER INSPECTING APPARATUS

(75) Inventors: Muneo Maeshima, Mito; Kazuo Takeda, Tokorozawa; Shigeru Matsui, Hitachinaka, all of (JP)

(73) Assignee: Hitachi, Ltd., Tokyo (JP)

( * ) Notice: Under 35 U.S.C. 154(b), the term of this patent shall be extended for 0 days.

(21) Appl. No.: 09/219,873

(22) Filed: Dec. 24, 1998

(30) Foreign Application Priority Data

Dec. 26, 1997 (JP) .................................................... 9-359394

(51) Int. Cl.[7] .................................................. G01N 21/47
(52) U.S. Cl. ...................................... 356/237.1; 356/446
(58) Field of Search .......................... 356/237.1, 237.2, 356/237.5, 239.1, 446, 369

(56) References Cited

U.S. PATENT DOCUMENTS

| | | | |
|---|---|---|---|
| 3,814,946 | * 6/1974 | Takahashi et al. | 356/239.1 |
| 5,293,538 | * 3/1994 | Iwata et al. | 356/237.5 |
| 5,424,536 | * 6/1995 | Moriya | 356/369 |
| 5,936,726 | * 8/1999 | Takeda et al. | 356/237.2 |

FOREIGN PATENT DOCUMENTS 7-318500  12/1995  (JP) .
10-293102  * 11/1998  (JP) .
11-101624  * 4/1999  (JP) .

* cited by examiner

Primary Examiner—Richard A. Rosenberger
(74) Attorney, Agent, or Firm—Kenyon & Kenyon

(57) ABSTRACT

Disclosed is a wafer inspecting apparatus suitable to determine whether a scattering substance is a surface foreign matter or an internal defect even if the particle size of the scattering substance is smaller than the wavelength of irradiation rays used for inspection. The wafer is obliquely irradiated with irradiation rays at the Brewster angle, and scattered rays which are scattered from a scattering substance on or in the wafer are detected at and angle 0° and an angle of the Brewster angle or more by detectors. Then, it is determined whether the scattering substance is a surface foreign matter or an internal defect on the basis of a ratio between the intensities of the scattered rays detected by the detectors. The intensity of scattered rays which are scattered from a surface foreign matter and detected at an angle of the Brewster angle or more is larger than the intensity of scattered rays which are scattered from the foreign matter and detected at an angle 0°, and the intensity of scattered rays which are scattered from an internal defect and detected at an angle of the Brewster angle or more is smaller than the intensity of scattered rays which are scattered from the internal defect and detected at an angle 0°. This makes it possible to distinguish the surface foreign matter and the internal defect from each other.

24 Claims, 3 Drawing Sheets

WAFER INSPECTING APPARATUS

BACKGROUND OF THE INVENTION

The present invention relates to a wafer inspecting apparatus, and particularly to a wafer inspecting apparatus for inspecting crystal defects such as precipitates or stacking faults in a silicon wafer in such a manner as to distinguish the crystal defects from foreign matters adhering on the surface of the silicon wafer.

As the level of integration of LSIs (Large Scale Integrated Circuits) has been enhanced, there has arisen a large problem in terms of reduction in percent non-defective and reliability resulting from failures of MOS (Metal Oxide Semiconductor) transistors constituting main parts of the LSIs. The failures of MOS transistors are typically caused by dielectric breakdown of gate oxide films and excess leakage currents at junctions. That is to say, most of the failures of MOS transistors directly or indirectly result from crystal defects in silicon substrates. To be more specific, in an LSI fabrication process, if a crystal defect exists in a surface region, to be oxidized into a silicon oxide film, of a silicon substrate, then a structural defect is formed in the silicon oxide film, causing dielectric breakdown upon operation of the LSI; while if a crystal defect exists in a depletion layer of a junction, there occurs a large amount of a leakage current therein. In this way, the presence of a crystal defect in a surface region, in which elements are formed, of a silicon substrate is undesirable because such a crystal defect causes a failure of a MOS transistor. For this reason, measurement of these crystal defects is important in quality control of silicon crystals. In this case, it may be desirable that crystal defects in a wafer be measured in such a manner as to be distinguished from foreign matters on the surface of the wafer, because the countermeasure taken against crystal defects in the wafer is different from that taken against foreign matters on the surface of the wafer.

One method has been disclosed in Japanese Patent Laid-open No. Hei 7-318500. In this method, infrared rays are rendered incident on a silicon substrate in the direction perpendicular thereto, and scattered rays are detected at the Brewster angle of silicon with respect to an axis perpendicular to the surface for each polarized component, to detect internal defects and surface foreign matters in such a manner as to make a distinction therebetween. The principle of this method is based on the fact that in regard to the transmittance of scattered rays which are scattered from an internal defect to the surface of a silicon substrate, the dependence of the intensity of a detection signal of the scattered rays on the polarization direction becomes largest when the scattered rays are detected at the Brewster angle of silicon.

Another method has been reported by Moriya and others in Proceedings of the 44-th Joint Meeting on Applied Physics, No. 1, p. 312, 1997, in which surface foreign matters and internal defects are detected using obliquely incident irradiation rays. In this method, a scattering substance detected by irradiation of S-polarized rays is taken as a surface foreign matter, and a scattering substance detected by irradiation of P-polarized rays is taken as an internal defect.

A further method has been reported by Kurihara in Journal of Electronic Material, PP. 50 to 56, February, 1997. In this method, the surface of a wafer is irradiated with rays in the direction perpendicular thereto, and foreign matters and irregular defects on the surface of the wafer are detected in such a manner as to make a distinction therebetween on the basis of a difference in angle distribution of the scattered rays.

In addition, Japanese Patent Laid-open No. Hei 6-345662 has disclosed a method in which the surface to be detected is irradiated with two kinds of laser rays having different wavelengths, and the presence or absence of defects on the surface is determined on the basis of a correlation between signals of the different scattered rays having the different wavelengths and scattered from the defects.

The above-described methods in which it is determined, by making use of polarization of scattered rays, whether a detected scattering substance is a surface foreign matter or an internal defect has the following problems:

The first problem is that when an object to be detected is irradiated with S-polarized rays, the incident rays interfere with reflected rays from the surface of the object and thereby the reflected rays are shifted from the incident rays by a phase of 180°, to cause a phenomenon that the surface becomes dark. On the contrary, when an object to be detected is irradiated with P-polarized rays, such a phenomenon occurs little. Taking the phenomenon into account, when a foreign matter having a particle size larger than the wavelength of irradiation rays is irradiated with the irradiation rays, the intensity of scattered rays from the foreign matter in the case using S-polarized rays as the irradiation rays is larger than the intensity of scattered rays from the foreign matter in the case of using P-polarized rays as the irradiation rays. On the contrary, for a foreign matter having a particle size sufficiently smaller than the wavelength of irradiation rays, the intensity of scattered rays from the foreign matter in the case of using P-polarized rays as the irradiation rays is larger than the intensity of scattered rays from the foreign matter in the case of using S-polarized rays as the irradiation rays, because of the interference effect. Accordingly, even if the intensity of scattered rays from a scattering substance in the case of using P-polarized irradiation rays or the intensity of scattered rays of a P-polarized component from the scattering substance is larger than the intensity of scattered rays from the scattering substance in the case of using S-polarized irradiation rays or the intensity of scattered rays of an S-polarized component from the scattering substance, it cannot be determined that the scattering substance is an internal defect.

The second problem is that the polarization state of scattered rays from a scattering substance is changed depending on whether the material of the scattering substance is anisotropic or isotropic. For example, in the case where irradiation rays are scattered from a scattering substance having a particle size sufficiently smaller than the wavelength of the irradiation rays (measurement of microdefects are generally equivalent to the case), it is apparent from the Rayleigh scattering theory that the polarization direction of the scattered rays from the scattering substance is the same as the irradiation direction of the irradiation rays insofar as the material of the scattering substance is isotropic. Accordingly, in the case where the scattering substance is an isotropic internal defect, there occur only the scattered rays which are scattered in the same polarization direction as that of the irradiation rays. However, in the case where the scattering substance is an anisotropic internal defect, the polarization direction of the scattered rays from the scattering substance is changed depending on the degree of the anisotropy of the scattering substance.

In view of the foregoing, it is undesirable to generally adopt a method of distinguishing a surface foreign matter and an internal defect from each other by making use of polarization information of irradiation rays or scattered rays.

Next, the above-described method in which the surface of a wafer is irradiated with irradiation rays in the direction perpendicular thereto has a problem. In the vertical incidence of irradiation rays, all polarized components are parallel to the surface irrespective of the polarization direction of the irradiation rays, so that the irradiation rays interfere with reflected rays irrespective of the polarization direction. Such interference between the irradiation rays and reflected rays makes small the intensity of the irradiation rays on the surface. This makes it difficult to detect a micro-defect.

SUMMARY OF THE INVENTION

An object of the present invention is to provide a wafer inspecting apparatus which is suitable to determine whether a scattering substance is a surface foreign matter or an internal defect even if the particle size of the scattering substance is smaller than the wavelength of irradiation rays used for inspection.

Another object of the present invention is to provide a wafer inspecting apparatus which is suitable to determine whether a scattering substance is a surface foreign matter or an internal defect even if the material of the scattering substance is either isotropic or anisotropic.

To achieve the above object, according to an aspect of the present invention, there is provided a wafer inspecting apparatus for obliquely irradiating a wafer with rays and detecting scattered rays which are from the wafer, including: a first scattered ray detecting system for detecting the scattered rays from the wafer; and a second scattered ray detecting system for detecting the scattered rays from the wafer; wherein the first scattered ray detecting system is disposed in a first direction where the intensity of scattered rays which are scattered from a foreign matter adhering on the surface of the wafer and detected by the first scattered ray inspecting system is larger than the intensity of scattered rays which are scattered from the foreign matter and detected by the second scattered ray inspecting system, and the intensity of scattered rays which are scattered from an internal defect of the wafer and detected by the first scattered ray inspecting system is smaller than the intensity of scattered rays which are scattered from the internal defect and detected by the second scattered ray inspecting system; and the second scattered ray inspecting system is disposed in a second direction where the intensity of scattered rays which are scattered from a foreign matter adhering on the surface of the wafer and detected by the second scattered ray inspecting system is smaller than the intensity of scattered rays which are scattered from the foreign matter and detected by the first scattered ray inspecting system, and the intensity of scattered rays which are scattered from an internal defect of the wafer and detected by the second scattered ray inspecting system is larger than the intensity of scattered rays which are scattered from the internal defect and detected by the first scattered ray inspecting system; whereby the foreign matter and the internal defect are distinguished from each other by comparing the intensity of the scattered rays detected by the first scattered ray inspecting system with the intensity of the scattered rays detected by the second scattered ray inspecting system.

According to another aspect of the present invention, there is provided a wafer inspecting apparatus for obliquely irradiating a wafer with irradiation rays and detecting scattered rays which are scattered from the wafer, including: a first scattered ray inspecting system for detecting scattered rays which are scattered from the wafer at an angle of the reflection angle of the irradiation rays or more; and a second scattered ray inspecting system for detecting scattered rays which are scattered from the wafer at an angle less than the reflection angle of the irradiation rays; whereby the internal defect and the foreign matter are distinguished from each other by comparing the intensity of the scattered rays detected by the first scattered ray inspecting system with the intensity of the scattered rays detected by the second scattered ray inspecting system.

According to a further aspect of the present invention, there is provided a wafer inspecting apparatus for obliquely irradiating a wafer with irradiation rays and detecting scattered rays which are scattered from the wafer, including: a first scattered ray inspecting system for detecting scattered rays which are scattered from the wafer at an angle of the Brewster angle or more; and a second scattered ray inspecting system for detecting scattered rays which are scattered from the wafer at an angle less than the Brewster angle; whereby the internal defect and the foreign matter are distinguished from each other by comparing the intensity of the scattered rays detected by the first scattered ray inspecting system with the intensity of the scattered rays detected by the second scattered ray inspecting system.

The wafer inspecting apparatus having the above configuration is suitable to determine whether a scattering substance is a surface foreign matter or an internal defect even if the particle size of the scattering substance is smaller than the wavelength of irradiation rays used for inspection.

The wafer inspecting apparatus having the above configuration is also suitable to determine whether a scattering substance is a surface foreign matter or an internal defect even if the material of the scattering substance is either isotropic or anisotropic

DETAILED DESCRIPTION OF THE PREFERRED EMBODIMENTS

Figure 1:
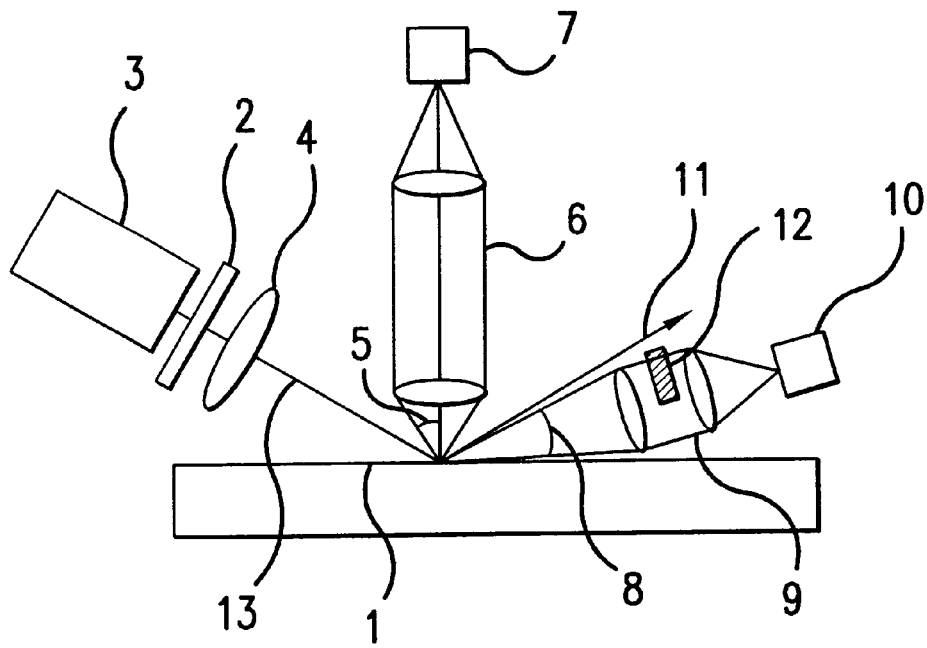
FIG. 1 is a diagram of an optical system illustrating the principle of one embodiment of a wafer inspecting apparatus of the present invention.

FIG. 1 shows an optical system illustrating the principle of one embodiment of a wafer inspecting apparatus of the present invention. It should be noted that the optical system shown in FIG. 1 is different from that of a type in which a foreign matter and an internal defect are distinguished from each other by comparing scattered rays from a scattering substance in the case of using P-polarized irradiation rays with scattered rays from the scattering substance in the case of using S-polarized irradiation rays and also the optical system does not adopt the vertical irradiation method.

Referring to FIG. 1, second harmonic rays emitted from an irradiation light source 3 composed of a YAG laser having a wavelength of 532 nm is rendered incident on a polarizer 2, and P-polarized component rays obtained from the polarizer 2 is converged, as irradiation rays 13, on the surface of a silicon wafer 1 configured as a sample through a condenser lens 4. The incident angle of the irradiation rays 13 is set at about 75° which is equivalent to the Brewster angle of silicon. The reason why the P-polarized rays rendered incident at the Brewster angle is used as irradiation rays is that the use of the P-polarized rays is lower in terms of a loss in intensity of the irradiation rays than the use of S-polarized rays as the irradiation rays. Such a requirement, however, is not indispensable but it is only a desirable requirement.

Specular reflection rays 11 are produced from the wafer 1, and also scattered rays are produced from the surfaces and interiors of crystals of the wafer 1. Of the scattered rays scattered in an angle range of the Brewster angle (about 75°) or less with respect to an axis perpendicular to the surface of the wafer 1, those scattered in an angle range 5 are converged at and detected by a detector 7 through a scattered ray detecting optical system 6. Meanwhile, of the scattered rays scattered in an angle range of more than the Brewster angle, those scattered in an angle range 8 are converged at and detected by a detector 10 through a scattered ray detecting optical system 9.

In the case of detecting scattered rays by the detector 10, the efficiency of detecting scattered rays from an internal defect is small because of the effect of total reflection of the scattered rays at the inner surface of the wafer 1, while scattered rays from a surface foreign matter are detected in the direction where the differential scattering cross-section becomes larger. That is to say, in detection of scattered rays by the detector 10, the detecting efficiency of scattered rays from a surface foreign matter is larger than that of scattered rays from an internal defect. On the other hand, in the case of detecting scattered rays by the detector 7, scattered rays from a surface foreign matter are detected in the direction where the differential scattering cross-section becomes smaller, while scattered rays from an internal defect are detected in the direction where the differential scattering cross-section becomes larger because the incident rays are scattered backward from the internal defect as is apparent in consideration of refraction of the incident rays. That is to say, in detection of scattered rays by the detector 7, the detecting efficiency of scattered rays from an internal defect is larger than that of scattered rays from a surface foreign matter. As a result, an internal defect can be detected in such a manner as to be distinguished from a surface foreign matter by determining that a scattering substance from which irradiation rays are scattered is an internal defect when a ratio S1/S2 (S1 and S2 are signals obtained by the detectors 7 and 10, respectively) is more than a threshold value, and by determining that the scattering substance is a surface foreign matter when the ratio S1/S2 is equal to or less than the threshold value.

While described later in another embodiment, the detection may be made using two kinds of rays having two wavelengths as irradiation rays. In this case, the above two wavelengths are selected such that the penetration depth in a wafer of the rays having one wavelength is three times or more larger or smaller than that of the rays having the other wavelength. With this selection of the two wavelengths of the two kinds of rays, in a depth range in which the rays having the shorter wavelength can penetrate, the attenuation rate of the rays having the longer wavelength becomes about 50%. As a result, it can be estimated from the Rayleigh scattering theory that an error occurring in calculating the particle size of a scattering substance on the basis of a signal of scattered rays having the longer wavelength and scattered from the scattering substance (particle size is proportional to [intensity of scattered rays]$^{1/6}$) is within 10% or less.

Figure 2:
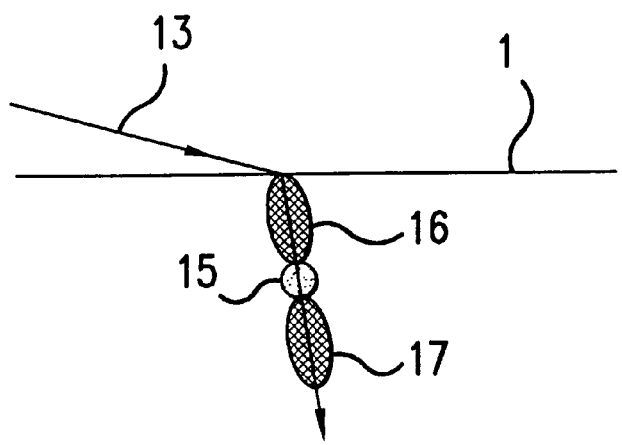
FIG. 2 is a diagram showing directions of scattered rays from an internal defect of a wafer when the wafer is irradiated with irradiation rays by an irradiation optical system shown in FIG. 1.

FIG. 2 shows directions of scattered rays from an internal defect 15 when the wafer 1 is irradiated with the irradiation rays 13 by the irradiation optical system shown in FIG. 1. Of the scattered rays, forward scattered rays 17 are not returned to the outside of the wafer 1 again. Of backward scattered rays 16, those scattered at an angle larger than a critical angle (about 14.5°) at the interface between the silicon wafer and air are totally reflected within the silicon wafer and thereby do not reach the outside of the wafer 1, and only those scattered at an angle smaller than the critical angle pass through the interface between the silicon wafer and air and are detected outside the silicon wafer.

Figure 3:
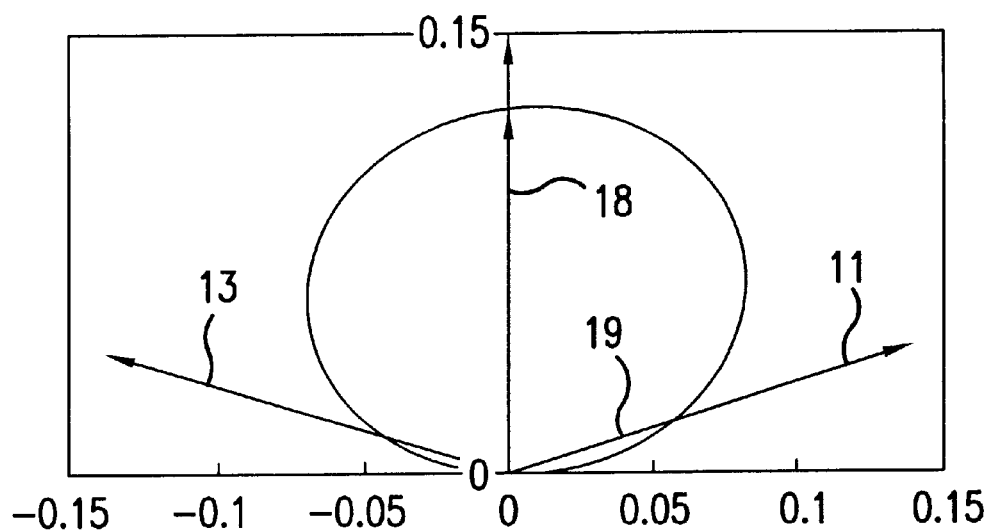
FIG. 3 is a diagram showing directions of components, detected by detectors provided outside a wafer, of scattered rays from an internal defect in the wafer.

FIG. 3 shows directions of those, detected outside the silicon wafer, of scattered rays from an internal defect of the silicon wafer. Referring to FIG. 3, an intensity 18 of those, detected at a detecting angle of 0°, of the scattered rays from the internal defect is as large as about 2.2 times an intensity 19 of those, detected in the reflection direction (75° in this case), of the scattered rays from the internal defect.

Figure 4:
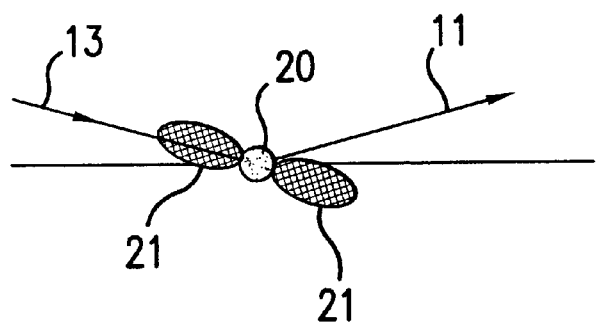
FIG. 4 is a diagram showing directions 21 of scattered rays from a foreign matter on the surface of a wafer when the wafer is irradiated with irradiation rays by the irradiation optical system shown in FIG. 1.

FIG. 4 shows directions 21 of scattered rays from a surface foreign matter 20 of a wafer 1 when the wafer 1 is irradiated with irradiation rays 13 by the irradiation optical system shown in FIG. 1. Of the scattered rays, those traveling in the wafer are reflected from the surface of the wafer.

Figure 5:
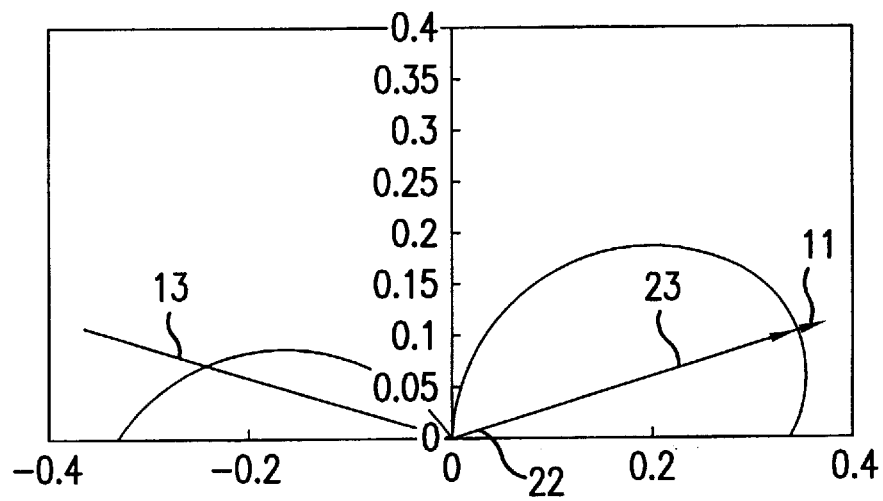
FIG. 5 is a diagram showing directions of scattered rays from a foreign matter on the surface of a wafer, which directions take into account the scattering of the scattered rays on the surface of the wafer.

FIG. 5 shows directions of scattered rays from a surface foreign matter. The directions take into account the scattering of the scattered rays on the surface of the wafer. Referring to FIG. 5, an intensity 22 of those, detected at a detecting angle 0°, of the scattered rays from the surface foreign matter is as small as about 0.067 times an intensity 23 of those, detected in the reflecting direction of the irradiation rays (75° in this case), of the scattered rays from the surface foreign matter.

Accordingly, an internal defect and a surface foreign matter can be detected in such a manner as to be distinguished from each other on the basis of a ratio between signals outputted from the detectors 7 and 10 shown in FIG. 1. Such detection is effective even if the particle size of a scattering substance is smaller than the wavelength of irradiation rays or even if the material of a scattering substance is either isotropic or anisotropic.

While the incident angle of irradiation rays in the above-described optical system is set at 75°, it may be set at a value being as small as nearly close to zero (equivalent to vertical incidence). In this case, those, reflected from the surface of a sample, of irradiation rays are returned substantially in the direction perpendicular thereto. The reflected rays obstruct measurement of weak scattered rays from a scattering substance, and therefore, to avoid detection of the reflected rays, the scattered ray inspecting system is formed with a hole which allows irradiation rays to pass therethrough but which does not allow the reflected rays to be converged therethrough. After convergence, only the scattered rays may be reflected using the perforated mirror to change the optical path thereof, to thereby perform the detection for each wavelength of irradiation rays. Also, as shown in FIG.

1, a mask 12 may be provided in order that the scattered ray inspecting optical system 9 avoids the reflected rays.

To avoid the reflected rays, the detector 7 may be not disposed on the plane perpendicular to the wafer containing the irradiation rays 13 and the reflected rays 11, and similarly the detector 10 may be not disposed on the plane perpendicular to the wafer including the irradiation rays 13 and the reflected rays 11.

The scanning of irradiation rays over the entire silicon wafer can be spirally performed by irradiating, with irradiation rays, the silicon wafer rotated with its center being subjected to translation motion. In this case, pulsive scattered rays occur at the instant a scattering substance passes through the irradiation region.

Figure 6:
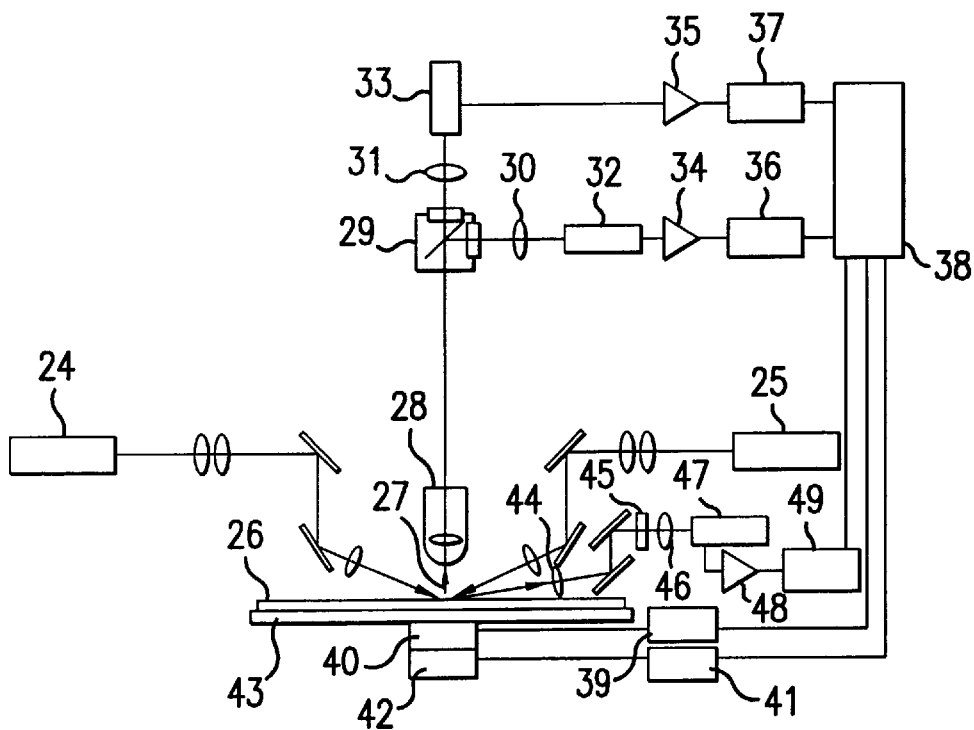
FIG. 6 is a conceptional diagram of another embodiment of the wafer inspecting apparatus of the present invention, in which different laser rays having two wavelengths are used as irradiation rays.

FIG. 6 shows a wafer inspecting apparatus as another embodiment of the present invention in which laser rays (wavelength: 532 nm) emitted from a laser 24 and laser rays (wavelength: 810 nm) emitted from a laser 25 are used as irradiation rays.

In the above wafer inspecting apparatus, crystal defects such as oxygen-containing precipitates ($SiO_2$ particles) and dislocations contained in a wafer 26 and foreign matters adhering on the surface of the wafer 26 are detected as scattering substances by irradiating the same point on the wafer 26 with the two kinds of irradiation rays and detecting scattered rays scattered from the scattering substances.

In a scattered ray inspecting system including an objective lens 28, scattered rays 27 from a defect are converged through the objective lens 28 and branched by a dichroic mirror 29 into scattered rays (wavelength: 532 nm) and scattered rays (wavelength: 810 nm). The scattered rays (wavelength: 532 nm) and scattered rays (wavelength: 810 nm) thus separated are respectively converged through lenses 30 and 31 and detected by detectors 32 and 33. The scattered ray inspecting system including the objective lens 28 is configured such that the intensity of scattered rays from a foreign matter on the surface of the wafer is smaller than that detected by a scattered ray inspecting system including a lens 44 to be described later and the intensity of scattered rays from an internal defect is larger than that detected by the scattered ray inspecting system including the lens 44. Such a scattered ray inspecting system may be called a scattered ray inspecting system which detects scattered rays at a detecting angle of the reflection angle 7° or less of the irradiation rays, or a scattered ray inspecting system which detects scattered rays at a detecting angle of the Brewster angle of silicon or less. Detection signals of the scattered rays (wavelength: 532 nm) and scattered rays (wavelength: 810 nm) detected by the detectors 32 and 33 are respectively amplified by amplifiers 34 and 35 and converted by A/D converters 36 and 37 into digital signals which are in turn inputted in a computer 38.

The scattered ray inspecting system including the lens 44 is configured such that the intensity of scattered rays from a foreign matter adhering on the surface of a solid is larger than that detected by the scattered ray inspecting system including the objective lens 28 and the intensity of scattered rays from an internal defect is smaller than that detected by the scattered ray inspecting system including the objective lens 28. Such a scattered ray inspecting system may be called a scattered ray inspecting system which detects scattered rays at a detecting angle of the reflection angle or more of the irradiation rays or a scattered ray inspecting system which detects scattered rays at a detecting angle of the Brewster angle or more. In this inspecting system, scattered rays scattered toward the lens 44 are converged through the lens 44, and are rendered incident on a filter 45. The filter 45 is designed to select only the scattered rays having the wavelength of 532 nm. The scattered rays thus selected are converged at and detected by a detector 47 through a lens 46. A signal outputted from the detector 47 is amplified by an amplifier 48, and converted by an A/D converter 49 into a digital signal which is in turn inputted in the computer 38.

In the wafer inspecting apparatus shown in FIG. 6, the intensities of the scattered rays detected by the detectors 32, 33 and 47 are converted into digital signals and inputted in a memory of the computer 38 only when the intensity of the signal of the scattered rays (wavelength: 532 nm) detected by the detector 32, that is, the intensity of the signal of the scattered rays detected by the inspecting system including the objective lens 28 is more than a predetermined threshold value. An in-plane position of the silicon wafer 26 at which scattered rays are produced is recorded together with the intensity of the scattered rays. The intensities of the scattered rays detected by the detectors 32, 33 and 47 may be converted into digital signals and inputted in the memory of the computer 38 only when the intensity of the signal of the scattered rays detected by the detector 47 is more than a predetermined threshold value. The intensities of the scattered rays detected by the detectors 32, 33 and 47 may be converted into digital signals and inputted in the memory of the computer 38 only when the scattered ray inspecting system including the objective lens 28 and the scattered ray inspecting system including the lens 44 detect signals of scattered rays whose intensities are more than predetermined threshold values, respectively. The intensities of the scattered rays detected by the detectors 32, 33 and 47 may be converted into digital signals and inputted in the memory of the computer 38 only when either the scattered ray inspecting system including the objective lens 28 or the scattered ray inspecting system including the lens 44 detects a signal of scattered rays whose intensity is more than a predetermined threshold value.

In this case, a ratio S1/S2 is calculated, where S1 is the intensity of the signal of the scattered rays detected by the scattered ray inspecting system including the objective lens 28 and the detector 32, and S2 is the intensity of the signal of the scattered rays detected by the scattered ray inspecting system including the lens 44 and the detector 47. Using the ratio S1/S2, it is determined that the detected scattering substance is an internal defect when the ratio S1/S2 is more than a predetermined threshold value, and it is determined that the detected scattering substance is a surface foreign matter when the ratio S1/S2 is equal to or less than the threshold value. To distinguish a surface foreign matter and an internal defect from each other, a ratio S3/S2 may be used, where S3 is the intensity of the signal of the scattered rays having the longer wavelength and detected by the scattered ray inspecting system including the objective lens 28 and the detector 33. In this case, it is determined that the detected scattering substance is an internal defect when the ratio S3/S2 is more than a predetermined threshold value, and it is determined that the detected scattering substance is a surface foreign matter when the ratio S3/S2 is equal to or less than the threshold value.

The measurement of scattered rays is performed by scanning a rotational stage 40 and an R stage 42 in the rotational direction (direction θ) and in the radial direction (direction R) using drivers 39 and 41 on the basis of commands supplied from the computer 38, respectively while monitoring coordinates (R, θ) of a rotational encoder and a translational encoder mounted to a wafer fixing jig 43. In this way, the coordinate (R, θ) obtained at the instant scattered rays from a defect are detected is inputted, together with the signal of the intensity of the scattered rays, in the computer 38.

In the above irradiation state, measurement may be performed by shifting the irradiation position by the rays (wavelength: 532 nm) from that by the rays (wavelength: 810 nm) so that a defect is earlier irradiated with the rays (wavelength: 810) than the defect is irradiated with the rays (wavelength: 532 nm) during scanning. In this case, both signals detected using the rays (wavelength: 532 nm) and the rays (wavelength: 810 nm) are inputted in the computer 38 only when the signal of the intensity of scattered rays (wavelength: 810 nm), that is, the intensity of the signal detected by the detector 33 is more than a predetermined threshold value. Since a defect whose depth position can be determined is within the penetration depth of the rays (wavelength: 532 nm), the depth position of the defect is measured only when the intensity of the signal of scattered rays (wavelength: 532 nm), that is, the intensity of the signal detected by the detector 32 is more than a predetermined value. As described above, to calculate the particle size of a scattering substance with an error kept in a range of 10%, two kinds of rays having two wavelengths which are selected such that the penetration depth of the rays having one wavelength is three times or more larger or smaller than that of the rays having the other wavelength are used as irradiation rays. The calculation of the particle size of a scattering substance may be concretely performed by a method wherein the particle size of each of a foreign matter on the surface of a wafer or a crystal defect in the wafer is calculated using the intensity of a signal of scattered rays having the long wavelength; the particle size of a scattering substance distinguished from the surface of the wafer is calculated using the intensity of a signal of scattered rays having the short wavelength; and the particle size of a scattering substance distinguished from the interior of the solid is calculated using the intensity of a signal of scattered rays having the long wavelength.

What is claimed is:

1. A wafer inspecting apparatus for obliquely irradiating a wafer with rays and detecting rays which are scattered from the wafer, and are caused by foreign matter adhering to the surface of the wafer and by internal defects in the wafer comprising:

a first scattered ray detecting system for detecting the scattered rays from the wafer; and a second scattered ray detecting system for detecting the scattered rays from the wafer;

wherein said first scattered ray detecting system is disposed in a first direction where the intensity of scattered rays which are scattered from foreign matter adhering on the surface of the wafer and detected by said first scattered ray inspecting system is larger than the intensity of scattered rays which are scattered from the foreign matter and detected by said second scattered ray inspecting system, and the intensity of scattered rays which are scattered from an internal defect of the wafer and detected by said first scattered ray inspecting system is smaller than the intensity of scattered rays which are scattered from the internal defect and detected by said second scattered ray inspecting system;

said second scattered ray inspecting system is disposed in a second direction where the intensity of scattered rays which are scattered from a foreign matter adhering on the surface of the wafer and detected by said second scattered ray inspecting system is smaller than the intensity of scattered rays which are scattered from the foreign matter and detected by said first scattered ray inspecting system, and the intensity of scattered rays which are scattered from an internal defect of the wafer and detected by said second scattered ray inspecting system is larger than the intensity of scattered rays which are scattered from the internal defect and detected by said first scattered ray inspecting system and;

a comparator comparing the intensity of the scattered rays detected by said first scattered ray inspecting system with the intensity of the scattered rays detected by said second scattered ray inspecting system to distinguish the foreign matter and the internal defects from each other.

2. A wafer inspecting apparatus for obliquely irradiating a wafer with rays and detecting rays which are scattered from the wafer, and are caused by foreign matter adhering to the surface of the wafer and by internal defects in the wafer comprising:

a first scattered ray detecting system for detecting scattered rays from the wafer; and a second scattered ray detecting system for detecting scattered rays from the wafer;

wherein said irradiation rays are composed of two kinds of rays having two wavelengths which are selected such that the penetration depth in the wafer of said rays having one wavelength is three times or more larger or smaller than that of rays having the other wavelength;

wherein with respect to at least one kind of said two rays having said two wavelengths, said first scattered ray detecting system is disposed in a first direction where he intensity of scattered rays which are scattered from a foreign matter adhering on the surface of the wafer and detected by said first scattered ray inspecting system is larger than the intensity of scattered rays which are scattered from the foreign matter and detected by said second scattered ray inspecting system, and the intensity of scattered rays which are scattered from an internal defect of the wafer and detected by said first scattered ray inspecting system is smaller than the intensity of scattered rays which are scattered from the internal defect and detected by said second scattered ray inspecting system, said second scattered ray inspecting system is disposed in a second direction where the intensity of scattered rays which are scattered from a foreign matter adhering on the surface of the wafer and detected by said second scattered ray inspecting system is smaller than the intensity of scattered rays which are scattered from the foreign matter and detected by said first scattered ray inspecting system, and the intensity of scattered rays which are scattered from an internal defect of the wafer and detected by said second scattered ray inspecting system is larger than the intensity of scattered rays which are scattered from the internal defect and detected by said first scattered ray inspecting system; and;

a comparator comparing the intensity of the scattered rays detected by said first scattered ray inspecting system with the intensity of the scattered rays detected by said second scattered ray inspecting system to distinguish the foreign matter and the internal defects from each other.

3. A wafer inspecting apparatus according to claim 2, wherein the particle size of the surface foreign matter is evaluated using said rays having the shorter one of said two wavelength, and the particle size of the internal defect is evaluated using said rays having the longer one of said two wavelengths.

4. A wafer inspecting apparatus according to claim 2, wherein it is determined that the internal defect or surface foreign matter is detected when the intensity of scattered rays detected by said first scattered ray inspecting system is more than a predetermined threshold value.

5. A wafer inspecting apparatus according to claim 2, wherein it is determined that the internal defect or surface foreign matter is detected when the intensity of scattered rays detected by said second scattered ray inspecting system is more than a predetermined threshold value.

6. A wafer inspecting apparatus according to claim 2, wherein it is determined that the internal defect or surface foreign matter is detected when the intensities of the scattered rays detected by said first and second scattered ray inspecting systems are more than predetermined threshold values, respectively.

7. A wafer inspecting apparatus according to claim 2, wherein it is determined that the internal defect or surface foreign matter is detected when the intensity of the scattered rays detected by said first or second scattered ray inspecting system is more than a predetermined threshold value.

8. A wafer inspecting apparatus for obliquely irradiating a wafer with rays and detecting rays which are scattered from the wafer, and are caused by foreign matter adhering to the surface of the wafer and by internal defects in the wafer comprising:
   a first scattered ray inspecting system or detecting scattered rays which are scattered from the wafer at an angle of the reflection angle of said irradiation rays and more;
   a second scattered ray inspecting system for detecting scattered rays which are scattered from the wafer at an angle less than the reflection angle of said irradiation rays;
   whereby the internal defect and the foreign matter are distinguished from each other by comparing the intensity of the scattered rays detected by said first scattered ray inspecting system with the intensity of the scattered rays detected by said second scattered ray inspecting system.

9. A wafer inspecting apparatus for obliquely irradiating a wafer with rays and detecting rays which are scattered from the wafer, and are caused by foreign matter adhering to the surface of the wafer and by internal defects in the wafer comprising:
   a first scattered ray detecting system for detecting scattered rays from the wafer; and
   a second scattered ray detecting system for detecting scattered rays from the wafer;
   wherein said irradiation rays are composed of two kinds of rays having two wavelengths which are selected such that the penetration depth in the wafer of said rays having one wavelength is three times or more larger or smaller than that of rays having the other wavelength;
   wherein with respect to at least one kind of said two rays having said two wavelengths,
   said first scattered ray inspecting system detects scattered rays which are scattered from the wafer at an angle of the reflection angle of said irradiation rays or more, and
   said second scattered ray inspecting system detects scattered rays which are scattered from the wafer at an angle less than the reflection angle of said irradiation rays; and;
   a comparator comparing the intensity of the scattered rays detected by said first scattered ray inspecting system with the intensity of the scattered rays detected by said second scattered ray inspecting system to distinguish the foreign matter and the internal defects from each other.

10. A wafer inspecting apparatus according to claim 9, wherein the particle size of the surface foreign matter is evaluated using said rays having the shorter one of said two wavelength, and the particle size of the internal defect is evaluated using said rays having the longer one of said two wavelengths.

11. A wafer inspecting apparatus according to claim 9, wherein it is determined that the internal defect or surface foreign matter is detected when the intensity of scattered rays detected by said first scattered ray inspecting system is more than a predetermined threshold value.

12. A wafer inspecting apparatus according to claim 9, wherein it is determined that the internal defect or surface foreign matter is detected when the intensity of scattered rays detected by said second scattered ray inspecting system is more than a predetermined threshold value.

13. A wafer inspecting apparatus according to claim 9, wherein it is determined that the internal defect or surface foreign matter is detected when the intensities of the scattered rays detected by said first and second scattered ray inspecting systems are more than predetermined threshold values, respectively.

14. A wafer inspecting apparatus according to claim 9, wherein it is determined that the internal defect or surface foreign matter is detected when the intensity of the scattered rays detected by said first or second scattered ray inspecting system is more than a predetermined threshold value.

15. A wafer inspecting apparatus for obliquely irradiating a wafer with rays and detecting rays which are scattered from the wafer, and are caused by foreign matter adhering to the surface of the wafer and by internal defects in the wafer comprising:
   a first scattered ray inspecting system for detecting scattered rays which are scattered from the wafer at an angle of the Brewster angle or more;
   a second scattered ray inspecting system for detecting scattered rays which are scattered from the wafer at an angle less than the Brewster angle; and;
   a comparator comparing the intensity of the scattered rays detected by said first scattered ray inspecting system with the intensity of the scattered rays detected by said second scattered ray inspecting system to distinguish the foreign matter and the internal defects from each other.

16. A wafer inspecting apparatus for obliquely irradiating a wafer with rays and detecting rays which are scattered from the wafer, and are caused by foreign matter adhering to the surface of the wafer and by internal defects in the wafer comprising:
   a first scattered ray inspecting system for detecting scattered rays from the wafer;
   wherein said irradiation rays are composed of two kinds of rays having two wavelengths which are selected such that the penetration depth in the wafer of said rays having one wavelength is three times or more larger or smaller than that of said rays having the other wavelength; and
   wherein with respect to at least one kind of said two rays having said two wavelengths,
   said first scattered ray inspecting system detects scattered rays which are scattered from the wafer at an angle of the Brewster angle or more, and said second scattered ray inspecting system detects scattered rays which are scattered from the wafer at an angle less than the Brewster angle; and;

a comparator comparing the intensity of the scattered rays detected by said first scattered ray inspecting system with the intensity of the scattered rays detected by said second scattered ray inspecting system to distinguish the foreign matter and the internal defects from each other.

17. A wafer inspecting apparatus according to claim 16, wherein the particle size of the surface foreign matter is evaluated using said rays having the shorter one of said two wavelength, and the particle size of the internal defect is evaluated using said rays having the longer one of said two wavelengths.

18. A wafer inspecting apparatus according to claim 16, wherein it is determined that the internal defect or surface foreign matter is detected when the intensity of scattered rays detected by said first scattered ray inspecting system is more than a predetermined threshold value.

19. A wafer inspecting apparatus according to claim 16, wherein it is determined that the internal defect or surface foreign matter is detected when the intensity of scattered rays detected by said second scattered ray inspecting system is more than a predetermined threshold value.

20. A wafer inspecting apparatus according to claim 16, wherein it is determined that the internal defect or surface foreign matter is detected when the intensities of the scattered rays detected by said first and second scattered ray inspecting systems are more than predetermined threshold values, respectively.

21. A wafer inspecting apparatus according to claim 16, wherein it is determined that the internal defect or surface foreign matter is detected when the intensity of the scattered rays detected by said first or second scattered ray inspecting system is more than a predetermined threshold value.

22. A wafer inspecting apparatus for obliquely irradiating a wafer with rays and detecting rays which are scattered from the wafer, and are caused by foreign matter adhering to the surface of the wafer and by internal defects in the wafer comprising:

a first scattered ray inspecting system for detecting scattered rays from the wafer; and a second scattered ray inspecting system for detecting scattered rays from the wafer;

wherein said irradiation rays are composed of two kinds of rays having first and second wavelengths which are selected such that the penetration depth in the wafer of said rays having said first wavelength is three times or more larger or smaller than that of said rays having said second wavelength and said first scattered ray inspecting system is adapted to detect the scattered rays having said first wavelength and scattered from the wafer and said second scattered ray inspecting system is adapted to detect the scattered rays having said second wavelength and scattered from the wafer;

wherein said first scattered ray detecting system is disposed in a first direction where the intensity of scattered rays which are scattered from a foreign matter adhering on the surface of the wafer and detected by said first scattered ray inspecting system is larger than the intensity of scattered rays which are scattered from the foreign matter and detected by said second scattered ray inspecting system, and the intensity of scattered rays which are scattered from an internal defect of the wafer and detected by said first scattered ray inspecting system is smaller than the intensity of scattered rays which are scattered from the internal defect and detected by said second scattered ray inspecting system, said second scattered ray inspecting system is disposed in a second direction where the intensity of scattered rays which are scattered from a foreign matter adhering on the surface of the wafer and detected by said second scattered ray inspecting system is smaller than the intensity of scattered rays which are scattered from the foreign matter and detected by said first scattered ray inspecting system, and the intensity of scattered rays which are scattered from an internal defect of the wafer and detected by said second scattered ray inspecting system is larger than the intensity of scattered rays which are scattered from the internal defect and detected by said first scattered ray inspecting system; and;

a comparator comparing the intensity of the scattered rays detected by said first scattered ray inspecting system with the intensity of the scattered rays detected by said second scattered ray inspecting system to distinguish the foreign matter and the internal defects from each other.

23. A wafer inspecting apparatus for obliquely irradiating a wafer with rays and detecting rays which are scattered from the wafer, and are caused by foreign matter adhering to the surface of the wafer and by internal defects in the wafer comprising:

a first scattered ray inspecting system for detecting scattered rays from the wafer; and a second scattered ray inspecting system for detecting scattered rays from the wafer;

wherein said irradiation rays are composed of two kinds of rays having first and second wavelengths which are selected such that the penetration depth in the wafer of said rays having said first wavelength is three times or more larger or smaller than that of said rays having said second wavelength;

wherein said first scattered ray inspecting system detects the scattered rays having said first wavelength and scattered from the wafer at an angle of the reflection angle of said irradiation rays or more, and said second scattered ray inspecting system detects the scattered rays having said second wavelength and scattered from the wafer at an angle of less than the reflection angle of said irradiation rays; and;

a comparator comparing the intensity of the scattered rays detected by said first scattered ray inspecting system with the intensity of the scattered rays detected by said second scattered ray inspecting system to distinguish the foreign matter and the internal defects from each other.

24. A wafer inspecting apparatus for obliquely irradiating a wafer with rays and detecting rays which are scattered from the wafer, and are caused by foreign matter adhering to the surface of the wafer and by internal defects in the wafer comprising:

a first scattered ray inspecting system for detecting scattered rays from the wafer; and a second scattered ray inspecting system for detecting scattered rays from the wafer;

wherein said irradiation rays are composed of two kinds of rays having first and second wavelengths which are selected such that the penetration depth in the wafer of said rays having said first wavelength is three times or more larger or smaller than that of said rays having said second wavelength;

wherein said first scattered ray inspecting system detects the scattered rays having said first wavelength and scattered from the wafer at an angle of the Brewster angle or more, and said second scattered ray inspecting system detects the scattered rays having said second wavelength and scattered from the wafer at an angle of less than the Brewster angle; and;

a comparator comparing the intensity of the scattered rays detected by said first scattered ray inspecting system with the intensity of the scattered rays detected by said second scattered ray inspecting system to distinguish the foreign matter and the internal defects from each other.

* * * * *